United States Patent [19]
Klardie et al.

[11] Patent Number: 6,142,296
[45] Date of Patent: *Nov. 7, 2000

[54] DENTAL IMPLANT PACKAGE

[75] Inventors: Michael Robert Klardie, Bloomington; Jeremy Matthew Huotari, Mound; Jean B. Christensen, Minneapolis; Peter B. Swenson, Eden Prairie, all of Minn.

[73] Assignee: Lifecore Biomedical, Inc., Chaska, Minn.

[*] Notice: This patent is subject to a terminal disclaimer.

[21] Appl. No.: 09/318,088

[22] Filed: May 25, 1999

Related U.S. Application Data

[63] Continuation of application No. 09/099,698, Jun. 19, 1998, Pat. No. 5,996,779.

[51] Int. Cl.[7] ................................................ A61B 19/02
[52] U.S. Cl. .................... 206/63.5; 206/368; 22/844; 22/831; 22/918
[58] Field of Search .................... 206/63.5, 368, 206/369, 339; 433/173, 174, 201.1; 215/350, 235; 220/843, 844, 831, 671, 737, 739, 921, 521, 918

[56] References Cited

U.S. PATENT DOCUMENTS

| | | | |
|---|---|---|---|
| 3,462,034 | 8/1969 | Friedberg | 215/350 |
| 4,712,681 | 12/1987 | Branemark et al. | |
| 4,763,788 | 8/1988 | Jorneus et al. | |
| 4,809,874 | 3/1989 | Pehr | 220/338 |
| 4,874,088 | 10/1989 | Leben | 206/387.1 |
| 4,934,556 | 6/1990 | Kleissendorf | 220/269 |
| 5,062,800 | 11/1991 | Niznick | 433/229 |
| 5,358,130 | 10/1994 | Mengeu et al. | 215/238 |
| 5,368,160 | 11/1994 | Leuschen et al. | 206/339 |
| 5,538,428 | 7/1996 | Staubli | 433/173 |
| 5,582,299 | 12/1996 | Lazzara et al. | 206/63.5 |
| 5,622,500 | 4/1997 | Niznick | 433/173 |
| 5,755,575 | 5/1998 | Biggs | 433/173 |
| 5,961,330 | 10/1999 | Hanson . | |

FOREIGN PATENT DOCUMENTS 0 669 111 A2  8/1995  European Pat. Off. .
0 669 111 A3  8/1995  European Pat. Off. .

OTHER PUBLICATIONS

"A new twist on reducing chair time . . . ", Spline Twist MP-1, SulzerMedica Sulzer Calcitek, Inc., brochure, Rev. Sep. 1998.

*Primary Examiner*—Paul T. Sewell
*Assistant Examiner*—Nhan T. Lam
*Attorney, Agent, or Firm*—Vidas, Arret & Steinkraus

[57] ABSTRACT

A dental implant package for supplying a dental implant and healing screw without impacting the sterility thereof is disclosed. The package comprises an elongated tubular housing with an open first end and a closed second end for receiving the dental implant and a cap for closing the tubular housing. The cap has a retainer therein for holding a healing screw and is constructed and arranged so that the cap in the fully open position presents the healing screw and dental implant side-by-side.

31 Claims, 3 Drawing Sheets

DENTAL IMPLANT PACKAGE

CROSS REFERENCE TO RELATED APPLICATION

This application is a continuation of U.S. application Ser. No. 09/099,698 filed Jun. 19, 1998, U.S. Pat. No. 5,996,779, the contents of which is incorporated herein in its entirety by reference.

BACKGROUND OF THE INVENTION

This invention relates to a sterilizable packaging for transporting dental implants and related components.

The use of dental implants is commonplace in the practice of dentistry. To minimize the risk of infection, it is necessary to sterilize an implant prior to placement. To avoid the need to sterilize implants in the dental office, a number of manufacturers now provide sterilized implants to the practitioner. In an effort to deliver these sterile dental implants to dentists a number of dental implant packages have been developed.

It is important when packaging a dental implant, that the implant be readily accessible and provided in a convenient presentation to the dentist. If the implant is not easily accessible, the dentist may compromise the sterility of the implant in an attempt to access it. The need for a convenient packaging becomes more acute where multiple components such as an implant and a healing screw are involved. Optimally, both components will be readily accessible to the dentist.

A number of dental implant packages have been developed. U.S. Pat. No. 4,763,788 to Jörnéus et al. discloses a hermetically sealed glass capsule enclosing an dental implant. The dental implant rests with an inner sleeve which is held in place in the capsule by a spring. The implant can only be accessed by breaking the glass capsule.

U.S. Pat. No. 5,062,800 to Niznick discloses a dental implant package including a two-part handle that can be attached to the implant inside of the package.

U.S. Pat. No. 5,582,299 to Lazzara et al. discloses a dental implant package in which, in one embodiment, a dental implant and a related component are presented side by side. In an alternate embodiment, a dental implant compartment is provided with a cover which includes a compartment for the related component. In this alternate embodiment, however, the implant and related component are not presented side by side.

There is a need for sterilizable dental implant package structures which, when opened, present the implant and a healing screw in an accessible side-by-side relationship.

SUMMARY OF THE INVENTION

The present invention is directed to a dental implant package for supplying a dental implant and healing screw side-by-side to a dental practitioner in a field. The package comprises an elongated tubular housing for receiving at least a portion of the dental implant. The housing has an open first end and a closed second end and the length of the elongated tubular housing exceeds that of the dental implant. The package further comprises a cap closing the first end of the elongated tubular housing. The cap is attached to the first end of the housing via a connector configured so that when the package is opened, the healing screw is presented to the practitoner side-by-side with the dental implant. The cap and elongated tubular housing further are constructed and arranged so that the healing screw and dental implant are enclosed within the package when the cap is closed. The cap also comprises a retainer for the healing screw. Optionally, the package may further comprise a removable inner sleeve resting within the elongated tubular housing and enclosing at least a part of the dental implant when the implant is present in the package.

The present invention is also directed to a closed, sterilized dental implant package comprising an elongated capsule having a first end with an opening therein and a second end which is closed. The elongated capsule receives at least a portion of the dental implant. The package also includes a cap for closing the first end of the capsule. The cap is connected to the elongated capsule by a connector. Together the cap and the elongated capsule encompass the dental implant and healing screw. The cap is constructed and arranged to present the healing screw alongside the implant when the cap is fully opened. The cap further comprises a retainer for the healing screw. The package optional comprises a removable inner sleeve for holding the dental implant. The removable inner liner rests in the elongated capsule and is supported by one or more optional sleeve stop surfaces therein. Finally, an optional base extends from the second end of the elongated capsule.

The present invention is also directed to an inventive package in combination with a dental implant and a healing screw and optionally closed and sterilized.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

Figure 1:
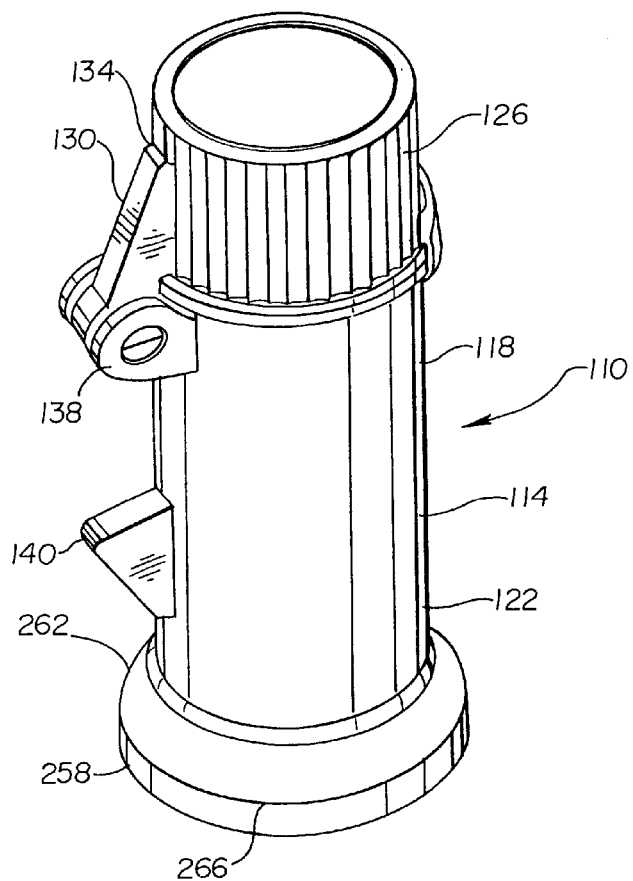
FIG. 1 shows a perspective view of the inventive dental implant package.
Figure 2:
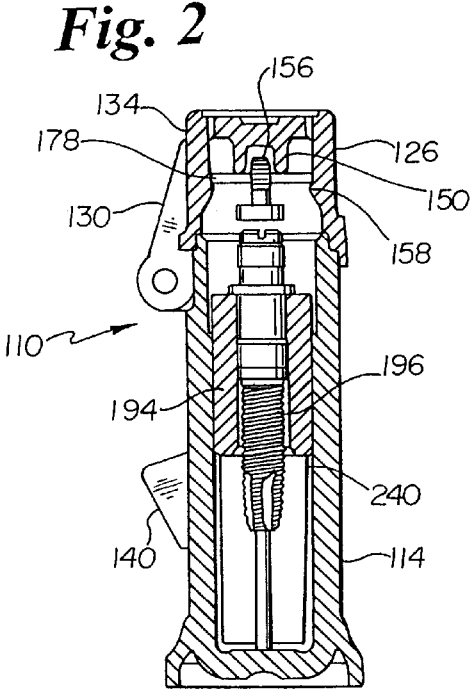
FIG. 2 shows a side elevational cut-away view of the dental implant package.
Figure 3:
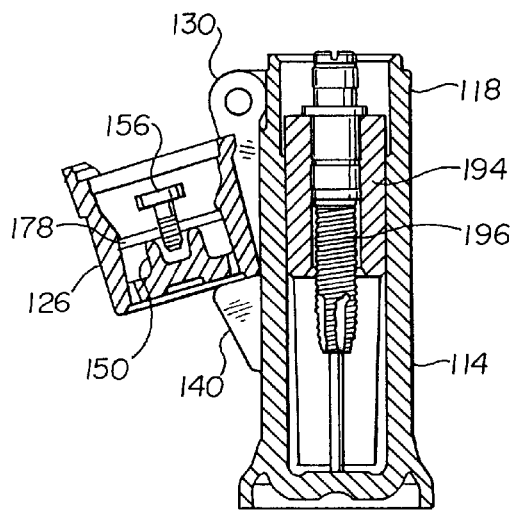
FIG. 3 shows a side elevational cut-away view of the dental implant package of FIG. 2, with the cap fully opened.

As shown in FIGS. 1–3, the inventive dental implant package, shown generally at 110, comprises an elongated tubular housing 114 having an open first end 118 and a closed second end 122. The elongated tubular housing has a length longer than the dental implant and is intended for receiving at least a portion of the dental implant.

Closing the first end 118 of tubular housing 114 is a cap 126 which, when removed from end 118 provides access to the implant located in elongated tubular housing 114. As shown in FIGS. 1–3, cap 126 is attached via a first hinge element 130 extending from exterior surface 134 of cap 126 and a second hinge element 138 extending from first end 118 of tubular housing 114. First hinge element 130 and second hinge element 138 cooperate so as to allow housing 114 to be opened at first end 118. Cap 126, elongated tubular housing 114 and hinge elements 130 and 138 are constructed and arranged so as to present a healing screw in a manner which allows for side-by-side access with a dental implant when cap 126 is removed from end 118 as shown in FIG. 3 and further to enclose the healing screw and dental implant within the dental implant package when cap 126 is on end 118, as shown in FIG. 2. Emanating from tubular housing 114 is a support surface 140 which is designed to provide support to cap 126 when healing screw 156 and dental implant 196 are presented side-by-side and pressure is applied to the cap, such as when a healing screw is removed therefrom.

Although cap 126 is shown attached to elongated housing 114 via a hinge structure, other forms of attachment are possible, for instance, a ball and socket joint or a flexible strip that is connected at one end to the cap and at the other end to the elongated housing.

Figure 4:
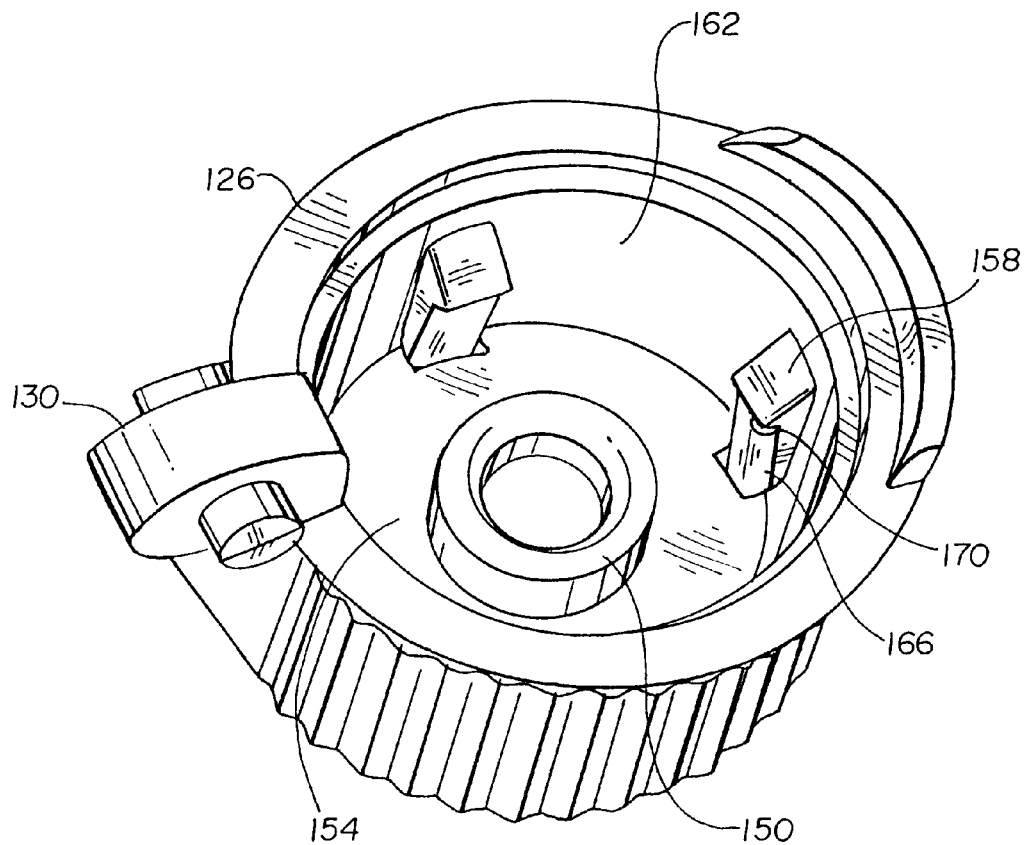
FIG. 4 shows a perspective view of the cap.
Figure 5:
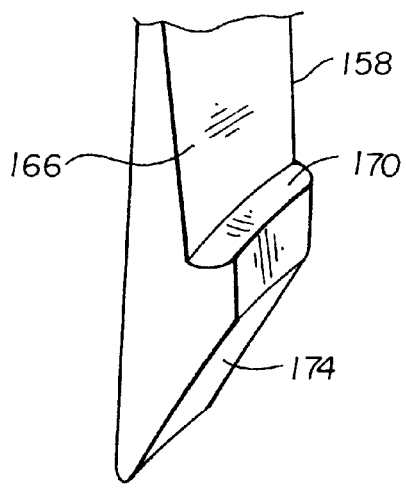
FIG. 5 shows a perspective view of a retainer stop surface in the cap.
Figure 6:
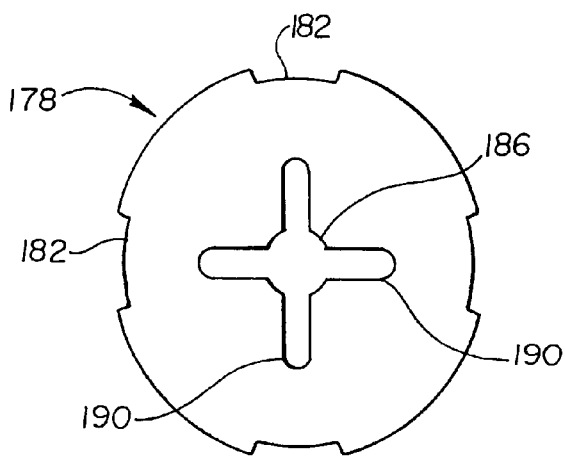
FIG. 6 shows a top view of the retainer in the cap.

Cap 126, as shown in FIG. 4, has a tubular section 150 emanating from the top 154 of the cap supporting a retainer 178 and holding at least a portion of healing screw 156. Four retainer stop surfaces 158 (two of which are shown, the remaining two situated opposite the two that are shown) emanate from the inner surface 162 of the cap. Retainer stop surfaces 158, as shown in FIG. 5, have a downward sloping first section 166, a shelf section 170 which is parallel to top 154 of cap 126 and a downward sloping second section 174. Shelf section 170 serves to hold a retainer shown generally at 178 in FIG. 6. While four retainer stop surfaces are depicted, the cap may have additional or fewer retainer stop surfaces.

Retainer 178 is substantially disk shaped and holds healing screw 156. Retainer 178 has a perimeter with notches 182 cut therein so as to cooperate with retainer stop surfaces 158 on the inner surface 162 of cap 126. For each retainer stop surface 158 there is a corresponding notch 182. Retainer 178 is held within cap 126 between tubular section 150 and shelf section 170 and further has a through-hole 186 through the center into which the healing screw is inserted. The diameter of through-hole 186 is such that the healing screw fits snugly therein. Retainer 178 has two perpendicular slots 190 extending through the center of the retainer to grip the healing screw. In other embodiments, more slots may be used. Retainer 178 is also arranged such that a bottom surface of the healing screw retained therein rests against the top 154 of cap 126 but within tubular section 150.

Figure 7:
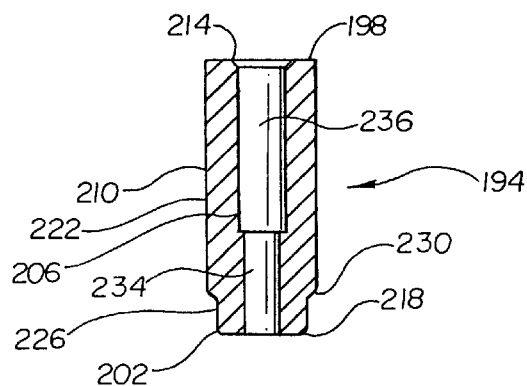
FIG. 7 shows a side elevational view of the removable inner sleeve in cross-section.

Dental implant package 110 may be provided with an optional removable inner sleeve, shown generally at 194 in FIG. 7, which rests within elongated tubular housing 114. Inner sleeve 194 is coaxial with tubular housing 114 and encloses at least a part of dental implant 196 when the implant is present in the package. Inner sleeve 194 has an annular top 198, an annular bottom 202, an inner surface 206 extending between annular top 198 and annular bottom 202 and an outer surface 210 extending between annular top 198 and annular bottom 202. A portion 214 of annular top 198 is optionally chamfered inward toward inner surface 206. Similarly, a portion 218 of annular bottom 202 is optionally chamfered toward outer surface 210 and a portion of annular bottom 202 may also be optionally chamfered inward toward inner surface 206.

The inner sleeve may have a constant outer diameter or may have one or more regions of differing diameter. The inner sleeve, as shown in FIG. 7 has an upper outer region 222 having a uniform first outer diameter and a lower outer region 226 having a uniform second outer diameter smaller than the first outer diameter. An optional chamfered outer transition region 230 extends between upper outer region 222 and lower outer region 226. Although chamfered outer transition region 230 is shown with a chamfer angle of about 45° relative to a horizontal reference plane, chamfer angles in a range of about 45° to about 90° are contemplated as well.

Further, inner sleeve 194 may have a constant inner diameter along the length of the sleeve or may have one or more regions of differing diameter. As shown in FIG. 7, inner sleeve 194 has an upper inner region 236 having a uniform first inner diameter and a lower inner region 234 having a uniform second inner diameter, the second inner diameter smaller than the first inner diameter. Although the inner diameter of the sleeve is shown as stepped, upper inner region 236 and lower inner region 234 may also be joined by a tapered region.

Figure 8:
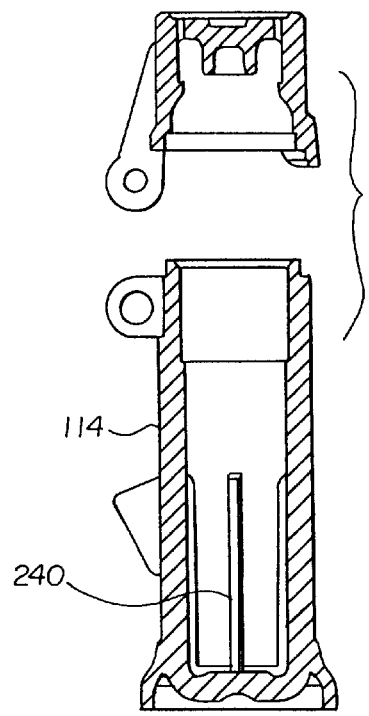
FIG. 8 shows side an elevational view of the elongated housing in cross-section.

Optional inner sleeve 194 is supported by one or more sleeve stop surfaces shown at 240 in FIG. 8 and disposed on the inner surface of elongated tubular housing 114. In a preferred embodiment, four or more sleeve support stop surface are present along the inner surface of elongated tubular housing 114.

Use of sleeves of different heights and/or internal configurations allows the package to be used with implants of different sizing and/or configurations.

Dental implant package 110 may further be provided with an optional base 258, as shown in FIG. 1, extending downward and/or outward from closed second end 122 of elongated tubular housing 114. Base 258 has a top 262 and a bottom 266 and is optionally chamfered from top 262 to bottom 266. Base 258 may be integrally formed with elongated tubular housing as one piece or may be fixedly attached to the bottom of the elongated tubular housing.

While a wide variety of materials are contemplated for the cap and elongated tubular housing, it is preferred that the cap and housing be formed of a transparent or nearly transparent material so that the practitioner can view at least a portion of the contents before opening the package. It is further desirable that the material be resistant to gamma radiation so that the package contents may be sterilized with gamma radiation at assembly. Suitable materials include treated polycarbonates such as Lexan™, Cycolac™, Valox™, Noryl™ and Ultem™. In a preferred embodiment, the cap and housing are made of HDPE (high density polyethylene) while the retainer is made of polystyrene.

The inner sleeve is preferably made of a biocompatible material such as titanium or an alloy thereof. It is desirable for the inner sleeve to be made of substantially the same material as the dental implant.

Figure 9:
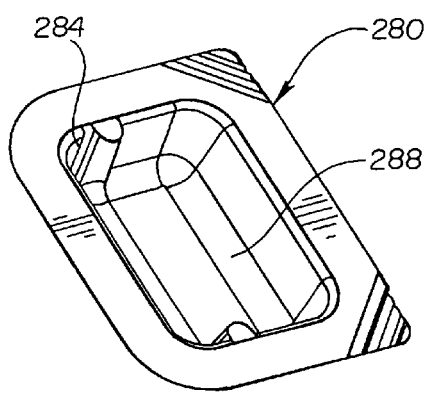
FIG. 9 shows a perspective view of an enclosure for holding the inventive packaging.
Figure 10:
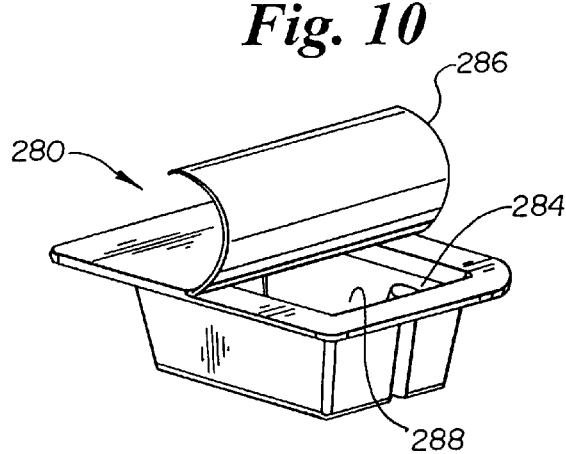
FIG. 10 shows the enclosure of FIG. 9 with the cover partially peeled away.

In FIGS. 9 and 10, the inventive dental implant package is carried within an enclosure, shown generally at 280, having a recess 288 therein for receiving the dental implant package. Adjacent to recess 288 is a second recess 284 into which additional material such as product literature may be inserted. Enclosure 280 further has a removable cover 286 for covering recess 284 and recess 288 when the dental implant package is disposed therein. Enclosure 280 is preferably made from a transparent or translucent material so that at least part of product literature contained within may be seen through the side of the enclosure. The removable cover may be made of a material such as Tyvek™.

The dental implant package may be furnished with a marking to indicate the size or type of the dental implant contained within. The cap may also be provided with a marking to indicate the size or type of the implant and healing screw contained within.

The above Examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A dental implant package comprising:
   a container having a first end with an opening therein and a closed second end, the container sized to receive at least a portion of a dental implant therein;
   a removable sleeve disposed in the container;
   a cap movably attached to the container, the cap having an opening therein sized to receive a healing screw therein;
   a retainer disposed within the cap for holding said healing screw;
   a connector movably attaching the cap and the container, the cap movable from a closed position in which the cap closes the first end of the container to an open position in which the cap is displaced from the first end of the container;
   the package presenting said healing screw and implant in side-by-side relationship when the cap is in the open position.

2. The dental implant package of claim 1 wherein the sleeve is sized to receive a dental implant therein.

3. The dental implant package of claim 2 comprising a dental implant disposed in the sleeve, wherein the sleeve prevents the dental implant from touching the container.

4. The dental implant package of claim 1 wherein the container is sized to contain the dental implant.

5. The dental implant package of claim 1 wherein the connector comprises a first hinge element extending from the cap and a second hinge element extending from the capsule, the first and second hinges elements mating with one another.

6. The dental implant package of claim 1 where the cap and container are formed of a material that is transparent.

7. A package for storing a dental implant and a healing screw, the package comprising:
   a container which is open at one end and closed at the other end and sized to contain a dental implant therein;
   a dental implant contained in the container;
   a cap which is sized to contain a healing cap therein and movably connected to the container;
   a healing screw contained within the cap, the healing screw comprising a head portion and a shaft portion;
   wherein the cap comprises a retainer which engages the shaft portion of the healing screw therein and
   wherein the cap may be moved from a first position in which it is disposed about the open end of the container to a second position in which it is disposed alongside the container, the healing screw snugly retained in the cap.

8. The package of claim 7 wherein the cap in the first position holds the healing screw in position above the dental implant, in a coaxial relationship.

9. The package of claim 8 wherein the cap in the second position holds the healing screw alongside the container.

10. The package of claim 9 wherein the healing screw is substantially inverted when the cap is moved from the closed position to the open position.

11. A dental implant package comprising:
    a container comprising a body with an opening therein, the container sized to receive a dental implant therein;
    a healing screw comprising a shaft portion;
    a cap,
      the cap comprising a top, a tubular outer wall extending from the top and a tubular inner wall extending from the top, the tubular outer wall disposed about the tubular inner wall and separated from the tubular inner wall by a gap, the cap comprising an opening therein sized for receiving the healing screw, the cap further comprising a retainer with an opening therein, a portion of the healing screw received therethrough,
      the cap attached to the container and movable from a closed position in which the cap closes the container to an open position in which the cap is in side-by-side relationship with the container;
    the retainer frictionally engaging the shaft portion of the healing screw, the healing screw retained within the cap by the retainer such that the healing screw remains in the cap as the cap is moved from a closed position to an open position, a portion of the healing screw received within the inner tubular wall; and
    a dental implant contained in the container.

12. The dental implant package of claim 11 wherein the container has a top end and a bottom end, the top end open and the bottom end closed, the bottom end of the container comprising a base which extends outward from the container.

13. The dental implant package of claim 12 wherein the base is chamfered.

14. The dental implant package of claim 11 where the cap and container are formed of a material that is transparent.

15. The dental implant package of claim 11 where the cap and container are formed of a material that is translucent.

16. The dental implant package of claim 11 wherein the cap and container are formed of a transparent material so that at least a portion of the contents of package is visible when the package is closed.

17. The dental implant package of claim 11 further comprising a removable sleeve resting within the container and coaxial with the container, the sleeve enclosing at least a part of the dental implant.

18. The dental implant package of claim 17 wherein the sleeve is made of a biocompatible material.

19. The dental implant package of claim 18 wherein the biocompatible material is an alloy of titanium.

20. The dental implant package of claim 11 wherein the cap and container are radiation transmissive.

21. The dental implant package of claim 11 wherein the cap and container are formed of a material that is resistant to gamma radiation.

22. A dental implant package comprising:
    a container comprising a body with an opening therein, the container sized to receive a dental implant therein;
    a cap,
      the cap comprising a top, a tubular outer wall extending from the top and a tubular inner wall extending from the top, the tubular inner wall having an upper surface disposed in a plane parallel to the top of the cap, the tubular outer wall disposed about the tubular inner wall and separated from the tubular inner wall by a gap, the tubular inner wall comprising an opening therein for receiving at least a portion of a healing screw, the cap attached to the container and movable from a closed position in which the cap closes the container to an open position in which the cap is in side-by-side relationship with the container, and a healing screw comprising a head portion and a shaft portion, the healing screw retained within the cap such that there is a gap between the head portion of the healing screw and the upper surface of the tubular inner wall.

23. A dental implant package comprising:

a container comprising a body with an opening therein, the opening sized to receive a dental implant therein;

a cap, the cap comprising a top, the cap comprising an opening therein for receiving a healing screw, the cap attached to the container and movable from a closed position in which the cap closes the container to an open position in which the cap is in side-by-side relationship with the container; and a healing screw comprising a head portion and a shaft extending therefrom, the healing screw disposed within the cap;

wherein the cap comprises a retainer disposed therein, the retainer frictionally engaging a portion of the shaft of the healing screw to retain the healing screw in the cap.

24. The dental implant package of claim 23 further comprising a dental implant received within the container.

25. The dental implant package of claim 23 formed of a transparent material.

26. The dental implant package of claim 23 further comprising a removable sleeve disposed about at least a portion of the dental implant.

27. A dental implant package comprising:

an elongated container comprising a first end with an opening therein and a second end which is closed, the elongated container sized to receive a dental implant therein;

a cap for closing the first end of the container, the cap comprising an opening therein sized for receiving a healing screw, the cap connected to the elongated container, the cap and the elongated container encompassing said dental implant and said healing screw, the cap further comprising a retainer for said healing screw;

the cap and container configured to present said healing screw received in the cap alongside said dental implant received in the container when the cap is fully opened; and a removable sleeve for holding said dental implant, the removable sleeve resting in the elongated container and supported by one or more stop surfaces in the container.

28. The dental implant package of claim 27 wherein the cap is connected to the container via a hinge.

29. The dental implant package of claim 27 further comprising a healing screw retained in the cap and a dental implant in the container.

30. The dental implant package of claim 27 further comprising a base extending outward from the second end of the elongated container.

31. A dental implant package comprising:

an elongated container comprising a first end with an opening therein and a second end which is closed, the elongated container sized to receive a dental implant therein;

a cap for closing the first end of the container, the cap comprising an opening therein sized for receiving a healing screw, the cap connected to the elongated container, the cap further comprising a retainer for a healing screw;

a healing screw received and retained in the cap;

a removable sleeve received in the container;

a dental implant received within the removable sleeve, the removable sleeve enclosing at least a part of the dental implant wherein the cap and container are configured to present the healing screw alongside an implant received in the container when the cap is fully opened and wherein the cap and the container encompass the dental implant and a healing screw.

* * * * *